United States Patent [19]

Williams et al.

[11] Patent Number: 4,681,969

[45] Date of Patent: Jul. 21, 1987

[54] PROCESS FOR THE PREPARATION OF AN ENANTIOMERIC PAIR OF ISOMERS OF CYFLUTHRIN

[75] Inventors: John Williams; Michael J. Robson, both of Berkshire, England

[73] Assignee: Imperial Chemical Industries PLC, London, England

[21] Appl. No.: 769,493

[22] Filed: Aug. 26, 1985

[30] Foreign Application Priority Data

Sep. 11, 1984 [GB] United Kingdom ............... 8422872

[51] Int. Cl.$^4$ .......................................... C07C 121/75
[52] U.S. Cl. ................................................... 558/407
[58] Field of Search ................... 260/465 D; 514/521; 558/407

[56] References Cited

U.S. PATENT DOCUMENTS

| 4,287,208 | 9/1981 | Fuchs et al. | 514/521 |
| 4,308,279 | 12/1981 | Smeltz | 514/521 |
| 4,544,508 | 10/1985 | Fuchs et al. | 260/465 D |

Primary Examiner—Dolph H. Torrence
Attorney, Agent, or Firm—Cushman, Darby & Cushman

[57] ABSTRACT

A process is described by which the pair of isomers represented by (R)-α-cyano-4-fluoro-3-phenoxybenzyl (1R,cis)-3-(2,2-dichlorovinyl)-2,2-dimethylcyclopropane carboxylate and its enantiomer is converted by base catalyzed epimerization in solution into the insecticidally more useful isomer pair represented by (S)-α-cyano-4-fluoro-3-phenoxybenzyl (1R,cis)-3-(2,2-dichlorovinyl)-2,2-dimethylcyclopropane carboxylate and its enantiomer, which may then be caused to crystallize out from the solution.

6 Claims, No Drawings

PROCESS FOR THE PREPARATION OF AN ENANTIOMERIC PAIR OF ISOMERS OF CYFLUTHRIN

This invention relates to a novel insecticidal product in the form of an enantiomeric pair of isomers of the compound cyfluthrin, and to insecticidal compositions and use thereof.

Cyfluthrin is the common name for the compound -α-cyano-4-fluoro-3-phenoxybenzyl 3-(2,2-dichlorovinyl)-2,2-dimethylcyclopropane carboxylate, which is described inter alia in published UK complete specification No. 1565932. It exists as a mixture of eight isomers some of which are described in European Patent Application No. 80103846.4 (Publication No. 0022970).

The present invention provides a novel insecticide product comprising just two isomers in the form of the racemate formed from (S)-α-cyano-4-fluoro-3-phenoxybenzyl (1R,cis)-3-(2,2-dichlorovinyl)-2,2-dimethylcyclopropanecarboxylate and its enantiomer, (R)-α-cyano-4-fluoro-3-phenoxybenzyl (1S,cis)-3-(2,2-dichlorovinyl)-2,2-dimethylcyclopropane carboxylate, substantially free from other isomers of the same compound, and hereinafter called 'The Racemate'.

The Racemate may be obtained by chromatographic separation from mixtures of isomers, e.g. from the product consisting of the eight isomers obtained by esterifying cis/trans-3-(2,2-dichlorovinyl)-2,2-dimethylcyclopropane carboxylic acid with (RS)-4-fluoro-3-phenoxybenzaldehyde cyanhydrin. This ester may also be prepared by reacting together 4-fluoro-3-phenoxybenzaldehyde with the acid chloride in the presence of an alkali metal cyanide, and water, optionally in the presence of a phase-transfer catalyst, e.g. an onium salt, such as tetraalkylammonium halide, and an organic solvent. A more convenient precursor for the Racemate may be obtained by reacting the 1RS, cis-acid chloride with the (R,S)-aldehyde and alkali metal cyanide. This product, consisting only of the four cis isomers is referred to hereinafter as 'The Starting Material'. It is itself a potent insecticide of greater relative efficacy than the previously described mixture of cis and trans isomers. However, The Racemate consisting of the two single isomers above mentioned is an even more effective insecticidal product.

By 'substantially free' as used herein is meant that the product containing the Racemate contains not more than 10% by weight of other isomers of the same compound.

The chromatographic separation of The Racemate may be accomplished using high performance liquid chromatographic means. A silica column is preferred, eluted with mixtures of an alkane, such as for example n-hexane, with a more polar material, such as an ester, for example ethyl acetate.

The Racemate may also be obtained in a crystalline form by a crystallisation technique.

This technique provides a process for obtaining a crystalline material (hereinafter called "the Product") consisting essentially of the enantiomeric pair of isomers represented by (S)-α-cyano-3-phenoxybenzyl (1R,cis)-3-(2,2-dichlorovinyl)-2,2-dimethylcyclopropane carboxylate and (R)-α-cyano-3- phenoxybenzyl (1S,cis)-3-(2,2-dichlorovinyl)-2,2-dimethylcyclopropane carboxylate in racemic proportions and substantially free from any other isomer of α-cyano-4-fluoro-3-phenoxybenzyl 3-(2,2-dichlorovinyl)-2,2-dimethylcyclopropane carboxylate, which comprises the steps of:

(a) forming a concentrated solution of The Starting Material with an organic solvent selected from lower alkanols containing up to 6 carbon atoms and liquid alkanes containing up to 8 carbon atoms, said solution containing from about 1:1 to about 1:4 parts by weight of the Starting Material:solvent, (b) adjusting the temperature of the solution to a temperature within the range $-10°$ C. to $25°$ C. and, optionally, adding a quantity of crystals of the enantiomeric pair of isomers to the solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and (e) optionally, if required, subjecting the crystalline material to recrystallisation.

By 'substantially free' is meant that not more than 10% by weight of the Product is represented by the combined weight of any other isomers.

Preferred alkanol solvents are ethanol, iso-propanol, butan-1-ol, butan-2-ol, pentan-1-ol, and iso-propanol/t-butanol (1:1), isopropanol/1,2-ethanediol (2:1). Isopropanol is particularly preferred. Preferred liquid alkane solvents are n-hexane and n-heptane.

By a concentrated solution is meant preferably one containing from 1:1 to 1:4, and most preferably 1:2, parts by weight of The Starting Material:solvent.

The Starting Material used in this process may be contaminated with up to 10% by weight of the corresponding trans isomers. Preferably Starting Material of at least 95% purity is used since this usually provides the Product in higher yield and purity.

The process may optionally be performed using a quantity of added crystals of the enantiomeric pair of isomers. This does not appear to be an absolute requirement to effect precipitation of the Product from the solution but it appears to enhance the rate at which crystallisation occurs, particularly if combined with agitation e.g. by stirring. A quantity of the enantiomer pair of isomers of sufficient purity to be added may be obtained by subjecting the Starting Material to high performance liquid chromatography (HPLC) as described above to separate the desired enantiomeric pair of isomers from the other isomers present.

The process is preferably conducted by preparing the solution using slight warming if necessary, and then cooling the solution to a temperature in the range $-10$ to $20°$ C. for a period within the range of about 10 hours to 10 days during which a substantial amount of Product crystallises. In a modified procedure the concentrated solution is added slowly to a mixture of the undissolved crystals and a little solvent, the rate of addition being adjusted to correspond with the rate of deposition of the Product. The period of addition may vary from a few hours to several days (e.g. up to 10) according to the volume of solution to be added.

The temperature at which the Product crystallises out is critical. At temperatures below $-10°$ C. the precipitate includes unwanted isomers; at temperatures above $25°$ C. no precipitation occurs at the concentrations used.

If recrystallisation is required to free the Product from other isomers which may have coprecipitated with the Product this may be achieved by using any suitable recrystallisation solvent, for example, the solvents referred to above as useful in the process for obtaining the Product.

The yield of Product may be substantially enhanced if at least step (c) of the above process is carried out in the presence of a base. This yield enhancement is the result of conversion by epimerisation of the enantiomeric pair of isomers represented by (R)-α-cyano-4-fluoro-3-phenoxybenzyl (1R,cis)-3-(2,2-dichlorovinyl)-2,2-dimethylcyclopropane carboxylate and (S)-α-cyano-4-fluoro-3-phenoxybenzyl (1S,cis)-3-(2,2-dichlorovinyl)-2,2-dimethylcyclopropane carboxylate to form in solution the enantiomeric pair of isomers represented by (S)-α-cyano-4-fluoro-3-phenoxybenzyl (1R,cis)-3-(2,2-dichlorovinyl)-2,2-dimethylcyclopropane carboxylate and (R)-α-cyano-4-fluoro-3-phenoxybenzyl (1s,cis)-3-(2,2-dichlorovinyl)-2,2-dimethylcyclopropane carboxylate, which is thereafter precipitated from solution as the Product.

In its simplest form this aspect of the invention provides a process for the relative enrichment of a solution of α-cyano-4-fluoro-3-phenoxybenzyl-3-(2,2-dichlorovinyl)-2,2-dimethyl cyclopropane carboxylate with respect to the enantiomeric pair of isomers represented by (S)-α-cyano-4-fluoro-3-phenoxybenzyl (1R,cis)-3-(2,2-dichlorovinyl)-2,2-dimethylcyclopropane carboxylate and (R)-α-cyano-4-fluoro-3-phenoxybenzyl (1S,cis-3-(2,2-dichlorovinyl)-2,2-dimethylcyclopropane carboxylate which comprises subjecting a solution comprising the enantiomeric pair of isomers (R)-α-cyano-4-fluoro-3phenoxybenzyl (1R,cis)-3-(2,2-dichlorovinyl)-2,2-dimethylcyclopropane carboxylate and (S)-α-cyano-4-fluoro-3-phenoxybenzyl (1S,cis)-3-(2,2-dichlorovinyl)-2,2-dimethylcyclopropane carboxylate to the action of a base to effect epimerisation.

Alcohols such as those specified above are suitable solvents for this process. Isopropanol is particularly preferred. The base may be any organic or inorganic base which is stable under the reaction conditions. Organic amines, especially secondary and tertiary amines, and heterocyclic bases are useful, for example triethylamine, diisopropylamine, dibutylamine, and 2,2,6,6-tetramethylpiperidine. Diisopropylamine is particularly preferred as it provides a high degree of epimerisation whilst minimising the amount of decomposition of The Starting Material during the process. This decomposition appears to be mainly due to base-catalysed transesterification reactions involving the solvent alcohol. Another useful base is 1H-1,5,9-triazabicyclo[4,4,0]dec-9-ene.

Also useful are inorganic bases such as alkali and alkaline earth metal hydroxides and carbonates, and alkali metal salts with weak organic acids such as acetic acid. Anhydrous potassium carbonate and potassium acetate are particularly preferred. Thus in one preferred embodiment of the process a solution of the Starting Material is passed through a column containing anhydrous potassium carbonate to effect the epimerisation.

The process is particularly useful to effect the enrichment of mother liquors from which the Product has been crystallised by the technique set out hereinabove. By the use of the combined enrichment and crystallisation processes all the Starting Material present may be effectively recovered in the form of the desired enantiomer pair.

In a further aspect therefore the invention provides an improved process for obtaining the Product which comprises the steps of:
(a) forming a concentrated solution of the Starting Material with an organic solvent selected from lower alkanols containing up to 6 carbon atoms and liquid alkanes containing from 5 to 8 carbon atoms, said solution containing from 1:1 to 1:4 parts by weight of the Starting Material:solvent,
(b) adjusting the temperature of the solution to a temperature within the range −10° C. to 25° C. and adding a quantity of crystals of the enantiomeric pair of isomers to the solution, the added crystals remaining thereafter in the solid undissolved state,
(c) maintaining the solution at a temperature within the said range for a sufficient period to allow the crystalline material to precipitate from the solution,
(d) separating the precipitated crystalline material from the solution, and
(e) optionally, if required, subjecting the crystalline material to recrystallisation, characterised in that a base is present during at least step (c) of the process whereby at least a proportion of the enantiomeric pair of isomers represented by (R)-α-cyano-4-fluoro-3-phenoxybenzyl (1R,cis)-3-(2,2-dichlorovinyl)-2,2-dimethylcyclopropane carboxylate and (S)-α-cyano-4-fluoro-3-phenoxybenzyl (1S,cis)-3-(2,2-dichlorovinyl)-2,2-dimethylcyclopropane carboxylate is converted to the enantiomeric pair of isomers represented by (S)-αcyano-4-fluoro-3-phenoxybenzyl (1R,cis)-3-(2,2-dichlorovinyl)-2,2-dimethylcyclopropane carboxylate and (R)-α-cyano-4-fluoro-3-phenoxybenzyl (1S,cis)-3-(2,2-dichlorovinyl)-2,2-dimethylcyclopropane carboxylate.

In a variation of this process the solution of Starting Material already containing the base may be added slowly to a stirred mixture of the seed crystals in a small amount of the solvent.

The Product is typically a white crystalline material with a melting point within the range 60°–67° C. Product with a purity of at least 99% with respect to the Racemate has a melting point of 66°–67° C. Since this is a higher melting point than that given in European Patent No. 22970 for the single isomer (S)-α-cyano-4-fluoro-3-phenoxybenzyl (1R,cis)-3-(2,2-dichlorovinyl)-2,2-dimethylcyclopropane carboxylate of 50°–52° C. it is clear that Product is a racemic compound in crystalline form, that is to say, that each individual crystal of the Product is composed of equal amounts of the two constituent isomers arranged regularly with respect to each other in a single crystal lattice. As such this represents an unexpectedly more thermodynamically stable material whose existence could not have been predicted, such a form having superior handling properties and formulation advantages over other products based on cyfluthrin, in addition to the advantage of superior insecticidal properties.

The Racemate may be used to combat the control infestations of insect pests and also other invertebrate pests, for example, acarine pests. The insect and acarine pests which may be combatted and controlled by the use of the Racemate include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the Racemate to the locus of the pests they are usually formulated into compositions which include in addition to the insecticidally active ingredient suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the Racemate is mixed with a solid diluent or carrier, for example kaolin, bentonite, kieselguhr, or talc, or they may be in the form of granules, wherein the Racemate is absorbed in a porous granular material for example pumice, gypsum or corn cob granules. Granules are particularly useful for combating soil borne insect pests, such as root worms of the genus Diabrotica, cutworms (Agrotis spp.) and wireworms (Agriotis spp.). Preferably, the granules contain from 1 to 2.5% by weight of the Racemate, which is absorbed onto the granule by, for example, spraying the granules with a solution of the Racemate in a volatile solvent which is subsequently evaporated from the surface of the granules. Such solutions may contain other ingredients, for example a resin to regulate the rate of release of the Racemate from the granules, or to help prevent premature disintegration of the granules. Granules may be applied to the soil either in a band between the furrows defining the crop rows, or broadcast, and may if desired be lightly incorporated in the soil, or they may be placed in the furrows themselves at the time of planting the crop. Application of granules at a rate of from 5 to 25 lb/acre (approximately 5 to 25 kg/ha) is usually sufficient to control the pests, and a preferred rate is within the range 8 to 15 lb/acre (approximately 8 to 15 kg/ha) based on the Racemate.

Alternatively the compositions may be in the form of liquid preparations to be used as dips or sprays, which are generally aqueous dispersions or emulsions of the Racemate in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation Products of ethylene oxide or propylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, and the condensation products of the said partial esters with ethylene oxide, propylene oxide and the lecithins.

The compositions may be prepared by dissolving the Racemate in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate containing a high proportion of the Racemate the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 1-85% by weight of the Racemate. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the Racemate is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Tetranychus cinnabarinus* (carmine spider mite)
Aonidiella spp. (scale insects)
Trialeuroides spp. (white flies)
*Blattella germanica* (cockroaches)
*Spodoptera littoralis* (cotton leaf worm)
*Chortiocetes terminifera* (locusts)
Diabrotica spp. (rootworms)
Agrotis spp. (cutworms)

The compounds of the invention and compositions comprising them have shown themselves to be particularly useful in controlling lepidopteran pests of cotton, for example Spodoptera spp. and Heliothis spp. The properties of the compounds enable them to be used to combat pests which inhabit the soil, for example Diabrotica spp. They may also be used optionally in conjunction with other insecticides to combat public health pests such as flies. They are also very useful in combating insect and acarine pests which infest domestic animals, such as *Lucilia sericata,* and ixodid ticks such as Boophilus spp., Ixodes spp., Amblyomma spp., Rhipicephalus spp., and Dermaceutor spp. They are effective in combatting both susceptible and resistant strains of these pests in their adult, larval and intermediate stages of growth, and may be applied to the infested host animal by topical, oral or parenteral administration.

The invention is illustrated by the following Examples.

In Examples 1 and 2 the isomers are identified by an abbreviated designation, e.g. 1R,cis-S which indicates that the isomer has the cis arrangement of hydrogen atoms in the cyclopropane ring with the (R) absolute stereochemistry at the 1-carbon, and (S) absolute stereochemistry at the α-carbon bearing the cyano group.

EXAMPLE 1

The higher activity of the Racemate is demonstrated by determining the $LC_{50}$ values (the concentration in parts per million (ppm) required to kill 50% of a population) for the economically important larval lepidopterous pest of cotton *Heliothis virescens* (tobacco budworm) for the Product and for cyfluthrin and some other isomer pairs. These are set out in the following table from which it can be seen that the Product is about four times more efficacious than cyfluthrin itself. The isomers were obtained by the h.p.l.c. technique shown in the next Example.

| ISOMER PAIR | $LC_{50}$ (ppm) |
| --- | --- |
| 1R,cis-S/1S,cis-R (the Product) | 1.8 |
| 1R,trans-S/1S,trans-R | 3.6 |
| 1S,cis-S/1R,cis-R | 23.4 |
| Cyfluthrin | 7.1 |

EXAMPLE 2

This Example illustrates the separation of (R,S)-α-cyano-4-fluoro-3-phenoxybenzyl (1R,S-cis)/(1R,S-trans)-3-(2,2-dichlorovinyl)-2,2-dimethylcyclopropane carboxylate (cyfluthrin) into its constituent enantiomeric pairs of isomers.

A sample of cyfluthrin (3.0 g) was cooled to 5° C. and triturated with petroleum ether (boiling range 40°–60° C., 20 cm³). The white solid component was removed by filtration and shown by analytical h.p.l.c. to consist of a mixture of 20% cis isomers and 80% trans isomers. This material (360mg) was subjected to h.p.l.c. (Gilson) using a silica column and eluting with a 1:1 (by volume) mixture of n-hexane and dichloromethane. Five fractions were collected, the second of which yielded the 1R,cis-S/1S,cis-R enantiomeric pair of isomers (36.5 mg) and the combined fourth and fifth fractions yielded a material consisting of 92% of trans isomers and 8% of cis isomers (218 mg). The trans isomers were tentatively identified as being in the form of the 1R,trans-S/1S,trans-R pair of enantiomeric isomers (hereinafter designated "Isomer pair T1"). The filtrate from the original trituration was also subjected to h.p.l.c. (Gilson) using the same conditions. Five fractions were obtained of which the third and fourth contained a mixture of all four pairs of enantiomeric isomers, and the fifth a mixture of the two enantiomeric pairs of trans isomers. The first and second fractions were combined and subjected to semi-preparative h.p.l.c. using 21 aliquots of 10 mg each and eluting with a 19:1 (by volume) mixture of n-hexane and diethyl ether. The first four fractions were collected, the first two being combined to yield 50 mg of the 1R-cis-R/1S,cis-S enantiomeric pair of isomers (hereinafter designated "Isomer pair C1") and the third and fourth fractions being combined to yield 36 mg of the 1R,cis-S/1S,cis-R enantiomeric pair of isomers ("Isomer pair C2").

The pairs of isomers were characterised by differences in their proton n.m.r. spectra (CDCl₃, tetramethylsilane standard) as follows:

| ENANTIOMERIC PAIR | N.M.R. (δ VALUES) |
| --- | --- |
| 1R,cis-S/1S,cis-R (Isomer Pair C2) | 1.20(d); 6.10(d); 6.32(s) |
| 1R,cis-R/1S,cis-S (Isomer Pair C1) | 1.30(s); 6.10(d); 6.25(s) |
| 1R,trans-S/1S,trans-R (Isomer pair T1) | 1.21(d); 5.57(d); 6.35(s) |

EXAMPLE 3

This Example illustrates the preparation of (RS) -α-cyano-4-fluoro-3-phenoxybenzyl (1RS,cis)-3-(2,2-dichlorovinyl)-2,2-dimethylcyclopropane carboxylate (The Starting Material).

A solution of sodium cyanide (5.9g) in water (19.1 cm³) containing 1% by weight of a wetting agent (sold under the name 'Synperonic' (Registered Trade Mark) and consisting essentially of an ethylene oxide condensate with 4-nonylphenol) was warmed to 35° C. and stirred whilst a mixture of (RS)-α-cyano-4-fluoro-3-phenoxybenzaldehyde (20.5 g), (1RS,cis)-1-chlorocarbonyl-3-(2,2-dichlorovinyl)-2,2-dimethylcyclopropane carboxylate (22.7 g) and dry toluene (60 cm³) was slowly added over a period of 1 hour, during which time the temperature of the reaction mixture was maintained within the range 35°–40° C. After the addition was complete the mixture was warmed to 40° C. for a further 4 hours and then kept at the ambient temperature for 16 hours. The mixture was diluted with diethyl ether, the organic layer separated and washed successively with water, brine, and saturated sodium bicarbonate solution and dried over anhydrous magnesium sulphate. Subsequent removal of the volatile solvents by evaporation under reduced pressure yielded an oil (43 g) which was shown by analytical h.p.l.c. to consist of a mixture of unreacted aldehyde (52.4%) and (RS)-α-cyano-4-fluoro-3-phenoxybenzyl (1RS,cis)-3-(2,2-dichlorovinyl)-2,2-dimethylcyclopropane carboxylate (46.6%). This oil was subjected to preparation h.p.l.c. (Gilson) using a loading of about 3 g aliquots and dichloromethane as eluent to yield the ester product as an oil (20.2 g, purity 94%) containing 45% by weight of the racemic pair of enantiomeric isomers represented by (S)-α-cyano-4-fluoro-3-phenoxybenzyl (1RS,cis)-3-(2,2-dichlorovinyl)-2,2-dimethylcyclopropane carboxylate and (R)-α-cyano-4-fluoro-3-phenoxybenzyl (1S,cis)-3-(2,2-dichlorovinyl)-2,2-dimethylcyclopropane carboxylate, and 55% by weight of the racemic pair of enantiomeric isomers represented by (R)-α-cyano-4-fluoro-3-phenoxybenzyl (1R,cis)-3-(2,2-dichlorovinyl)-2,2-dimethylcyclopropane carboxylate and (S)-α-cyano-4-fluoro-3-phenoxybenzyl (1S,cis)-3-(2,2-dichlorovinyl)-2,2-dimethylcyclopropane carboxylate.

EXAMPLE 4

A sample (1.5 g) of the Starting Material as prepared by the procedure illustrated in the previous Example was separated into its constituent racemic isomer pairs by the use of a Waters h.p.l.c. apparatus. The eluent was n-hexane (19 parts by volume and ethyl acetate (1 part by volume) applied at a pressure of 15 atmospheres at a rate of 300 cm³ min⁻¹. The Product was collected as an oil after two recycles as the second observed fraction-h.p.l.c. analysis indicated it contained 95% by weight of The Racemate and 5% by weight of the other pair of isomers. The oil was admixed with a small amount of a 1:1 mixture of petroleum ether (boiling range 40°–60° C.) and diethyl ether in a glass dish and induced to crystallise on scratching the dish with a glass rod. The Product was obtained as a white crystalline material, m.p. 61°–63.5° C.

EXAMPLE 5

This Example illustrates the base-catalysed epimerisation and crystallisation technique to obtain the Product. Three experiments were performed. The procedure was as follows. An amount of the Starting Material (ca. 1 g—obtained by the procedure illustrated in Example 3) was dissolved in dry isopropanol (dried by distillation from calcium hydride) containing 5% (by volume) of dry diisopropylamine at the ambient temperature (ca. 23° C.). To this was added a small quantity of the Product (ca. 5 mg) in the form of a slurry prepared by recrystallisation from isopropanol of the Product isolated in the previous Example. The mixture was kept at the ambient temperature for a period followed by a further period at a lower temperature. The crystallised Product was collected by filtration and warmed with a little petroleum ether (boiling range 40°–60° C.) at 0° C. and dried in a vacuum desiccator. The conditions and results obtained in the three experiments are set out in the following table:

|  | EXP. 1 | EXP. 2 | EXP. 3 |
|---|---|---|---|
| Wt. of Starting Material | 1.01 g | 1.00 g | 1.07 g |
| % purity | 94% | 94% | 94% |
| % Racemate present | 45% | 45% | 45% |
| Volume of isopropanol | 1.0 cm³ | 2.0 cm³ | 3.0 cm³ |
| Period/Temperature of crystallisation | 6.5 days/ 23° C. | 4 days/ 23° C. + 1 day/1° C. | 7 days/ 23° C. + 2 days/1° C. |
| Wt. of the Product obtained | 0.38 g | 0.50 g | 0.40 g |
| melting point | 66–67° C. | 65–67° C. | 65–66° C. |
| % Racemate Present | 97.1% | 96.8% | 91.0% |
| % Racemate present in residue obtained from filtrate | 51.7% | 46.1% | 47.2% |

We claim:

1. A process for obtaining an enhanced yield of a crystalline material consisting essentially of the enantiomeric pair of isomers represented by (S)-α-cyano-4-fluoro-3-phenoxybenzyl (1R,cis)-3-(2,2-dichlorovinyl)-2,2-dimethylcyclopropane carboxylate and (R)-α-cyano-4-fluoro-3-phenoxybenzyl (1S,cis)-3-(2,2-dichlorovinyl)-2,2-dimethylcyclopropane carboxylate in racemic proportions and substantially free from any other isomer of α-cyano-4-fluoro-3-phenoxybenzyl-3-(2,2-dichlorovinyl)-2,2-dimethylcyclopropane carboxylate, which comprises the steps of:

(a) Forming a concentrated solution of (RS)-α-cyano-3-phenoxybenzyl (1RS,cis)-3-(2,2-dichlorovinyl)-2,2-dimethylcyclopropane carboxylate which is free from trans isomer, with an organic solvent selected from lower alkanols containing up to six carbon atoms, (b) adjusting the temperature of the solution to a temperature within the range −10° C. to 25° C. and adding a quantity of crystals of the enantiomeric pair of isomers to the solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and (e) optionally, if required, subjecting the crystalline material to recrystallisation, characterised in that a base is present during at least step (c) of the process whereby at least a proportion of the enantiomeric pair of isomers represented by (R)-α-cyano-4-fluoro-3-phenoxybenzyl (1R,cis)-3-(2,2-dichlorovinyl)-2,2-dimethylcyclopropane carboxylate and (S)-α-cyano-4-fluorophenoxybenzyl (1R,cis)-3-(2,2-dichlorovinyl)-2,2-dimethylcyclopropane carboxylate is converted to the enantiomeric pair of isomers represented by (S)-α-cyano-4-fluoro-3-phenoxybenzyl (1R,cis)-3-(2,2-dichlorovinyl)-2,2-dimethylcyclopropane carboxylate and (R)-α-cyano-4-fluoro-3-phenoxybenzyl (1S,cis)-3-(2,2-dichlorovinyl)-2,2-dimethylcyclopropane carboxylate.

2. A process according to claim 1 wherein the organic solvent is a lower alkanol containing up to six carbon atoms.

3. A process according to claim 2 wherein the lower alkanol is isopropanol.

4. A process according to claim 1 wherein the base is secondary or tertiary amine or a heterocyclic base.

5. A process according to claim 4 wherein the base is diisopropylamine, 2,2,6,6-tetramethylpiperidine or 1H-1,5,9-triazabicyclo-[4,4,0]-dec-9-ene.

6. The process substantially according to claim 1 with the modification that the solution also contains the base and is added slowly to a mixture of the undissolved crystals of the enantiomeric pair of isomers and the organic solvent whilst maintaining the temperature within the range −10° to 25° C.

* * * * *